United States Patent
McCall, Jr. et al.

(10) Patent No.: US 11,857,768 B1
(45) Date of Patent: Jan. 2, 2024

(54) FILTERING NEEDLE ASSEMBLY WITH SEAL PLUG

(71) Applicant: CARRTECH Corp., Frederick, MD (US)

(72) Inventors: Charles Edward McCall, Jr., Fuquay-Varina, NC (US); Theodore Jay Mosler, Raleigh, NC (US); James Kevin Fentress, Athlone (IE); Megan Anderson Conley, Athlone (IE); Sue Ellen Carr, Dickerson, MD (US)

(73) Assignee: CARRTECH Corp., Frederick, MD (US)

( * ) Notice: Subject to any disclaimer, the term of this patent is extended or adjusted under 35 U.S.C. 154(b) by 0 days.

(21) Appl. No.: 18/220,736

(22) Filed: Jul. 11, 2023

Related U.S. Application Data

(63) Continuation of application No. PCT/US2022/045475, filed on Oct. 1, 2022.

(51) Int. Cl.
*A61M 5/31* (2006.01)
*A61M 5/34* (2006.01)

(52) U.S. Cl.
CPC ............ *A61M 5/3145* (2013.01); *A61M 5/34* (2013.01)

(58) Field of Classification Search
CPC ..... A61M 5/3145; A61M 5/34; A61M 5/3286
See application file for complete search history.

(56) References Cited

U.S. PATENT DOCUMENTS

| | | | |
|---|---|---|---|
| 2,775,240 A | 12/1956 | Morrisey, Jr. | |
| 2,827,081 A | 3/1958 | Little | |
| 2,833,281 A | 5/1958 | Krug | |
| 2,857,913 A | 10/1958 | Miskel | |
| 2,864,366 A | 12/1958 | Miskel | |
| 2,876,770 A | 3/1959 | White | |
| 2,972,991 A | 2/1961 | Burke | |
| 3,008,570 A | 11/1961 | Roehr | |
| 3,042,241 A | 7/1962 | Bauman | |
| 3,757,780 A | 9/1973 | Ishikawa | |
| 4,127,131 A | 11/1978 | Vaillancourt | |
| 4,137,917 A | 2/1979 | Cohen | |

(Continued)

FOREIGN PATENT DOCUMENTS

| CN | 106061547 B | 5/2020 |
|---|---|---|
| WO | 2014186800 A1 | 11/2014 |

OTHER PUBLICATIONS

Heo, Joo Hyung, PCT—Written Opinion of the International Searching Authority for PCT Patent Application No. PCT/US2022/045475, dated Jun. 26, 2023, 5 pages, Korean Intellectual Property Office, Daejeon, South Korea.

*Primary Examiner* — Tasnim Mehjabin Ahmed
(74) *Attorney, Agent, or Firm* — Kevin E Flynn; FLYNN IP LAW

(57) ABSTRACT

A filtering needle assembly for use in administering a liquid payload, including: a needle and connector portion; a filtering needle body cap; a seal plug, and a filter: The seal plug initially lacking a needle channel so that a distal end of a hollow needle must be forced through the distal end of the seal plug while the seal plug is retained by a holding tool with a hollow midline of adequate depth to receive the protruding end of the hollow needle. An attempt to reuse the filtering needle assembly with a second insertion of a hollow needle into the filtering needle assembly will not work as the distal end of the hollow needle will push the seal plug distally rather than traverse the seal plug.

17 Claims, 8 Drawing Sheets

(56) References Cited

U.S. PATENT DOCUMENTS

| | | |
|---|---|---|
| 4,180,071 A | 12/1979 | Oiwa |
| 4,273,123 A | 6/1981 | Lemelson |
| 4,316,462 A | 2/1982 | Baker |
| 4,365,626 A | 12/1982 | House |
| 4,617,012 A | 10/1986 | Vaillancourt |
| 4,725,267 A | 2/1988 | Vaillancourt |
| 4,747,831 A | 5/1988 | Kulli |
| 4,795,432 A | 1/1989 | Karczmer |
| 4,887,998 A | 12/1989 | Martin |
| 4,927,416 A | 5/1990 | Tomkiel |
| 4,935,016 A | 6/1990 | DeLeo |
| 4,998,924 A | 3/1991 | Ranford |
| 5,059,185 A | 10/1991 | Ryan |
| 5,064,418 A | 11/1991 | Cronin |
| 5,080,648 A | 1/1992 | D'Antonio |
| 5,156,599 A | 10/1992 | Ranford |
| 5,158,550 A | 10/1992 | Scholl, Jr. |
| 5,295,963 A | 3/1994 | Deeks |
| 5,312,370 A | 5/1994 | Talonn |
| 5,338,310 A | 8/1994 | Lewandowski |
| 5,601,536 A | 2/1997 | Crawford |
| 5,674,203 A | 10/1997 | Lewandowski |
| 5,735,823 A | 4/1998 | Berger |
| 5,746,727 A | 5/1998 | Graves |
| 5,795,336 A | 8/1998 | Romano |
| 5,879,337 A | 3/1999 | Kuracina |
| 6,287,278 B1 | 9/2001 | Woehr |
| 6,302,868 B1 | 10/2001 | Mohammad |
| 6,623,458 B2 | 9/2003 | Woehr |
| 6,629,959 B2 | 10/2003 | Kuracina |
| 6,629,962 B2 | 10/2003 | Correa |
| 6,679,864 B2 | 1/2004 | Gagnieux |
| 6,749,588 B1 | 6/2004 | Howell |
| 6,776,775 B1 | 8/2004 | Mohammad |
| 6,860,871 B2 | 3/2005 | Kuracina |
| 6,958,055 B2 | 10/2005 | Donnan |
| 7,306,740 B2 | 12/2007 | Freund |
| 7,632,243 B2 | 12/2009 | Bialecki |
| 7,749,190 B2 | 7/2010 | Griffiths et al. |
| D623,732 S | 9/2010 | Brady et al. |
| 7,811,261 B2 | 10/2010 | Rubinstein |
| 7,927,314 B2 | 4/2011 | Kuracina |
| 8,002,751 B2 | 8/2011 | Carr |
| 8,162,882 B2 | 4/2012 | Rubinstein |
| RE43,473 E | 6/2012 | Newby |
| 8,568,367 B2 | 10/2013 | Griffiths |
| 9,669,164 B2 | 6/2017 | Carr |
| 10,512,728 B2 | 12/2019 | Carr et al. |
| 10,568,810 B2 | 2/2020 | Lin et al. |
| 2005/0277893 A1 | 12/2005 | Liversidge |
| 2009/0227950 A1 | 9/2009 | Jensen |
| 2010/0042053 A1 | 2/2010 | Dillard, III |
| 2011/0319817 A1 | 12/2011 | Rubinstein |
| 2012/0289930 A1 | 11/2012 | Rubinstein |
| 2014/0261877 A1 | 9/2014 | Ivosevic |
| 2016/0317389 A1 | 11/2016 | Ivosevic |

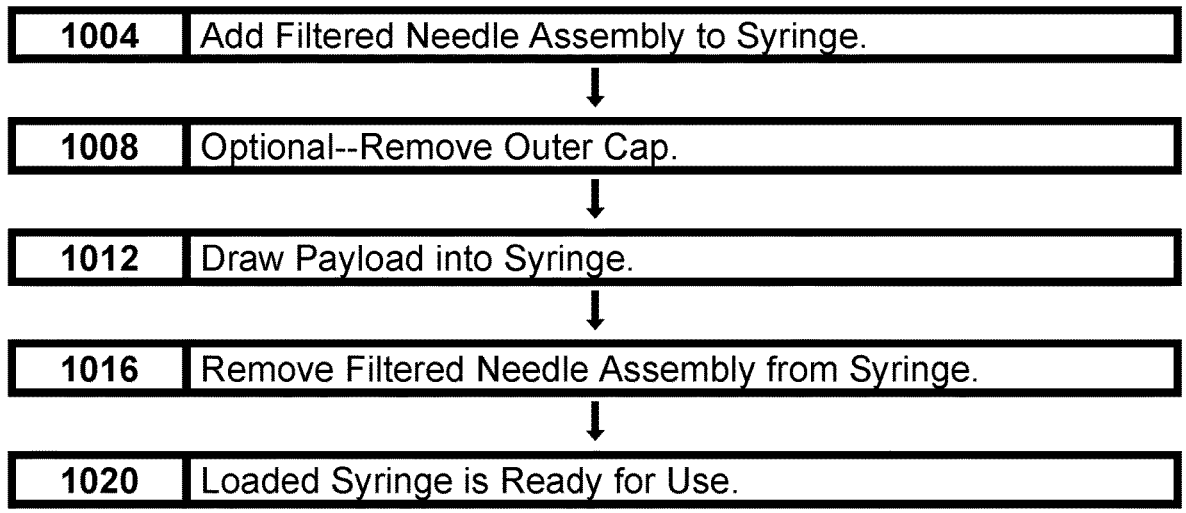

| 1004 | Add Filtered Needle Assembly to Syringe. |
| 1008 | Optional--Remove Outer Cap. |
| 1012 | Draw Payload into Syringe. |
| 1016 | Remove Filtered Needle Assembly from Syringe. |
| 1020 | Loaded Syringe is Ready for Use. |

FIG. 8   2000

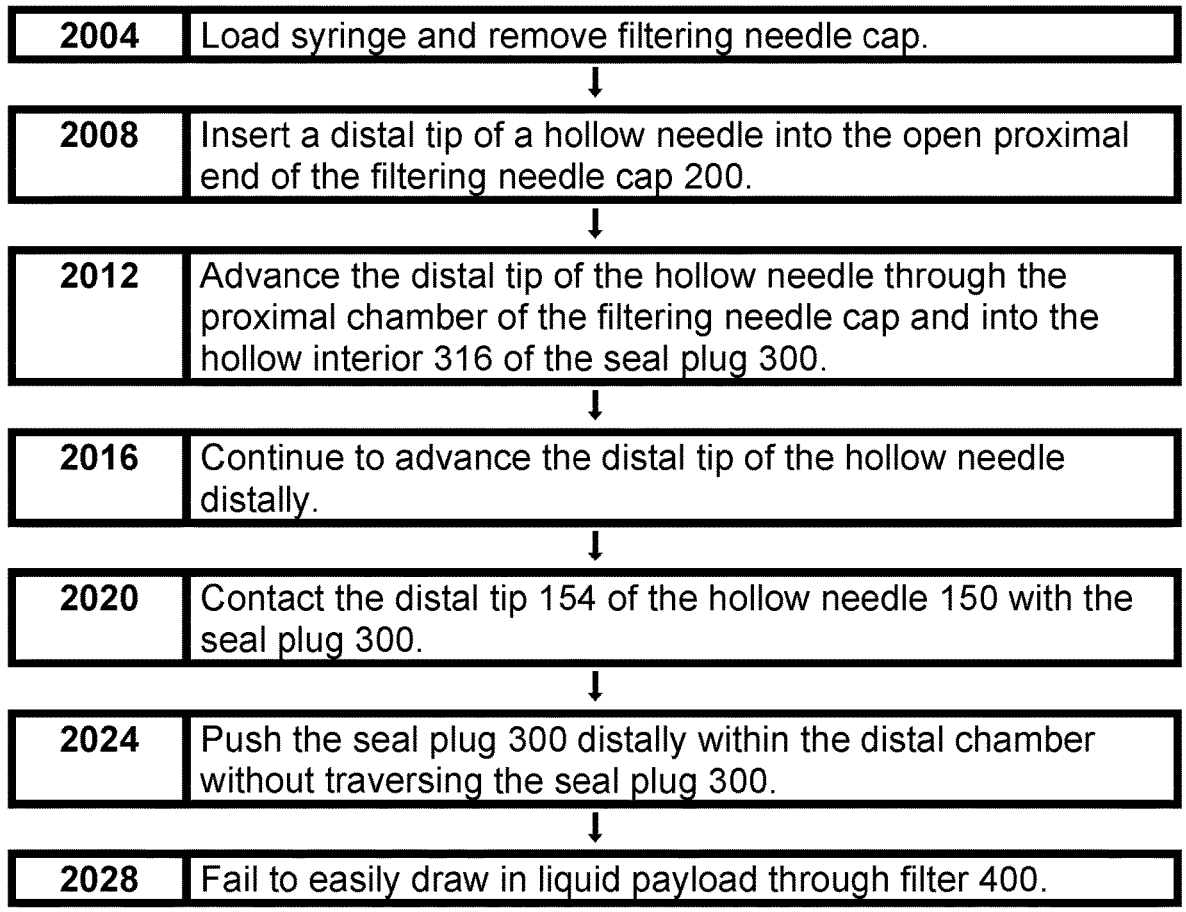

| 2004 | Load syringe and remove filtering needle cap. |
| 2008 | Insert a distal tip of a hollow needle into the open proximal end of the filtering needle cap 200. |
| 2012 | Advance the distal tip of the hollow needle through the proximal chamber of the filtering needle cap and into the hollow interior 316 of the seal plug 300. |
| 2016 | Continue to advance the distal tip of the hollow needle distally. |
| 2020 | Contact the distal tip 154 of the hollow needle 150 with the seal plug 300. |
| 2024 | Push the seal plug 300 distally within the distal chamber without traversing the seal plug 300. |
| 2028 | Fail to easily draw in liquid payload through filter 400. |

FIG. 10  3000

| 3004 | Obtain: the needle and connector portion 110; a filtering needle cap body 25, a seal plug 300, and a filter 400. |
|---|---|

↓

| 3008 | Push the seal plug 300 until the seal plug rests against the annular shoulder 220. |
|---|---|

↓

| 3012 | Hold the seal plug while the distal tip traverses the seal plug. |
|---|---|

↓

| 3016 | Remove the holding tool. |
|---|---|

↓

| 3020 | Insert the filter 400 into the distal end of the filtering needle cap body 250. |
|---|---|

↓

| 3024 | Creating a sealed and sterilized package with the filtered needle assembly 100 inside the package. |
|---|---|

FILTERING NEEDLE ASSEMBLY WITH SEAL PLUG

This application claims priority to co-pending and commonly assigned PCT Patent Application No. PCT/US2022/045475 for Filtering Needle Assembly with Seal Plug which was filed Oct. 1, 2022. The '475 is incorporated herein in its entirety. This application incorporates by reference commonly assigned U.S. Pat. No. 9,669,164 B2 for Filtering Needle Cap Having a Sealing Sleeve Around a Needle, issued Jun. 6, 2017. To the extent that the teachings or use of terminology found in the '164 patent differ from the present application, the usage in the present application controls.

BACKGROUND

Field of the Disclosure

This disclosure relates generally to a filter needle assembly for safely administering pharmaceuticals or other liquid payloads needing filtration before administration to a patient. The filter needle assembly may be used with human patients, veterinary uses for animals, and other uses that benefit from the filtering of a liquid payload before delivery. In this disclosure and the claims that follow, the term needle should be understood as a hypodermic needle or analogous needle with an open distal end and an interior lumen to allow for movement of a liquid.

Liquid pharmaceuticals are typically stored in sealed glass ampoules (often spelled ampule) or other known storage devices. In the case of glass ampoules, in order to gain access to the pharmaceuticals, the ampoule is opened by snapping the glass neck. In so doing, debris in the form of glass shards may be produced. The shards must be removed from the pharmaceuticals prior to administration. The debris is typically removed by drawing up the pharmaceutical through a filtered cannula or straw secured to the end of the syringe.

While the most common use of a syringe to deliver liquids is to deliver a liquid pharmaceutical, other liquid payloads can be drawn in from a reservoir through a filter to remove debris before delivering the filtered liquid payload through a needle connected to the syringe.

Examples of uses beyond pharmaceuticals include the injection of some nutraceuticals into a patient. Some public health organizations provide needle exchanges to people addicted to illegal drugs as a way to limit spread of disease and a filtered needle may be of benefit in this application. Some blood products such as PCC (Prothrombin Complex C) use a filtered needle. The list of uses should not be deemed a limitation to the scope of the claims as those of skill in the art will be able to adapt the teachings of the present disclosure for use with a particular liquid payload and need for filtration.

Methods for removing debris include a two-stage process and a one-stage process. In the two-stage process, a needle or straw has a filter element secured in the needle and connector portion. As the liquid payload is drawn up into the syringe, the filter traps the debris, removing it from the liquid payload to be administered. The filtered straw or needle is then removed from the syringe and discarded. In order to avoid inadvertent administration of contaminated liquid payload to the patient, care must be taken to remove and discard the filtered needle. In addition to the danger of mistakenly administering a contaminated liquid payload to a patient, the two-stage process may involve the use of specially adapted and costly disposable devices.

Relevant prior art includes commonly assigned U.S. Pat. No. 9,669,164 to Carr et al. issued Jun. 6, 2017 for Filtering Needle Cap Having Sleeve Sealing Around a Needle. This filtering needle cap featured a sleeve to seal around an outside diameter of the hollow needle inserted into the filtering needle cap from an open end towards the distal/filter end. The arrangement of the sleeve within the filtering needle cap limited a dead volume of liquid payload drawn through the filter into the filtering needle cap but not drawn into the distal tip of the hollow needle.

Commonly assigned U.S. Pat. No. 10,512,728 to Carr et al. issued Dec. 24, 2019 for Filtering Needle Cap with a Seal Around a Needle. The '728 patent is the result of a divisional application claiming priority to the '164 patent. The '728 had common objectives with the '164 patent but differed in that the '164 patent relied on a sleeve to seal a portion of the outer perimeter of the hollow needle and the '728 patent did not use a separate sleeve component. Instead the '728 taught an intermediate portion of the filtering needle cap between the distal open end of the filtering needle cap and the proximal open end of the filtering needle cap, the intermediate portion sized so that insertion of the distal tip of the hollow needle through the intermediate portion of the filtering needle cap substantially seals a perimeter around an outside diameter of the hollow needle closer to the distal end of the hollow needle than to the proximal end of the hollow needle when the filtering needle cap is attached to the hub, so that the liquid payload is drawn into the lumen in the hollow needle as the liquid payload is drawn into the fluid fitting and is impeded from traveling down the outside diameter of the hollow needle within the filtering needle cap.

Single-Use Medical Devices should be Used Just Once.

The filter needle assemblies are intended for a single use. The filtering needle cap taught in U.S. Pat. No. 9,669,164 (discussed above) or in U.S. Pat. No. 10,512,728 (discussed above) are intended for a single use. Once the hollow needle has been removed from the filtering needle cap, the filtering needle cap should be discarded. However, a filtering needle cap such as taught in the '164 or '728 patent could be reused as there is nothing to prevent reinsertion of the distal tip of the hollow needle back into the filtering needle cap and through the sleeve or sealing intermediate portion.

Even with prohibitions on the packaging and user instructions, there is always a temptation to reuse equipment. Sometimes this is an attempt to stretch budgets by using an item intended for single use a few times as there will be many needs to draw the same liquid payload from a series of identical ampules.

It is conceivable that a staff member obtained a filtering needle cap and used the filtering needle cap in the prescribed manner but after removing the hollow needle from the filter needle cap, the staff member wishes to draw up additional liquid payload from the ampule and does not want to go to the supply cabinet to obtain another filtering needle cap. Perhaps the staff member did not draw the full amount of liquid payload that is needed for the patient.

A second use may be harmless if there was no gap in time as the staff member immediately realized that the amount of liquid payload needed is more than the amount drawn into the syringe. But if the staff member set down the used filtering needle cap in a location that is not sterile, this is a problem. As the staff member has only two arms, it is more likely than not that the used filtering needle cap was set down somewhere.

The risks are much higher if the staff member is looking to provide additional liquid payload from a different ampule hours later and finds it easier to reuse a used filter needle cap rather than obtain a new filtering needle cap down the hall from the supply cabinet. It is not clear how often such a problem may arise, but the prior art including the '164 and the '728 patent does not preclude trying to get a second use out of a filtering needle cap.

The goal of precluding a second use of a single-use medical product is not unique to filter needle assemblies. See for example U.S. Pat. No. 5,261,880, issued Nov. 16, 1993 for Single Use Syringes with Second Use Lockout. The improvement patented in the '880 patent was modifying a single-use hypodermic syringe so the syringe locks up after one use.

Vocabulary.

A, An.

In this application, and the claims that follow, the terms a, an, or the identification of a single thing should be read as at least one unless such an interpretation is impossible within the context of the entirety of the specification. For example, the use of the terms sole, only, or the phrase not more than one would indicate that a single item is intended.

Chamber.

The term chamber is used below in order to describe portions of an interior pathway through which the liquid payload travels. While in some uses of the word chamber, the chamber may be sealed by closing doors (such as a bed chamber or the judge's chamber), in this context, a chamber is a partially enclosed space having an ingress and egress.

Gne and Gnes.

To avoid the awkward he/she and his/her or the potentially confusing singular use of they and their, this application uses the gender-neutral pronoun—gne, the possessive pronoun—gnes, reflexive pronoun—gneself, and the object form—gnerm.

Or.

Unless explicit to the contrary, the word "or" should be interpreted as an inclusive or rather than an exclusive or. Thus, the default meaning of or should be the same as the more awkward and/or.

Proximal and Distal.

The terms proximal and distal are commonly used when discussing medical devices. For the purposes of this application and the claims that follow, proximal means the end that is normally held by the end user and distal is the opposite end. Thus in the case of a hypodermic needle, the end of the needle injected into the patient or an IV bag would be the distal end and the syringe end manipulated by the user would be the proximal end. For the holding tool that holds the seal plug, the proximal end is the end inserted into the filter needle cap body to be consistent with deeming the syringe end of the assembly to be the proximal end.

Seal.

In the present disclosure and the claims that follow, the term seal is used as the teachings of the present disclosure call for creating a seal between the outer perimeter of the needle and the inner perimeter of an opening created in a seal plug so that the syringe may effectively draw the liquid payload through the interior of the needle without pulling air past the seal and into the open distal end of the needle. Likewise, there is a seal between the outside of the seal plug and the interior of the filter needle cap. A seal adequate for this purpose may not be a sufficient seal to maintain a more dramatic pressure differential across the seal or maintain a seal against a more moderate pressure gradient for a substantial period of time. Thus, in this context, the noun and verb seal indicate a seal sufficient to allow the syringe to draw in liquid payload.

Set.

Unless explicit to the contrary, the word "set" should be interpreted as a group of one or more items.

Step.

The term step may be used in descriptions within this disclosure. For purposes of clarity, one distinct act or step may be discussed before beginning the discussion of another distinct act or step. The term step should not be interpreted as implying any particular order among or between various steps disclosed unless the specific order of individual steps is expressly indicated.

Substantially.

Frequently, when describing an industrial process it is useful to note that a given parameter is substantially met. Examples may be substantially parallel, substantially perpendicular, substantially uniform, and substantially flat. In this context, substantially X means that for purposes of this industrial process it is X. So something that may not be absolutely parallel but is for all practical purposes parallel, is substantially parallel. Likewise, mixed air that has substantially uniform temperature would have temperature deviations that were inconsequential for that industrial process.

As recognized in C. E. Equipment Co. v. United States, 13 U.S.P.Q.2d 1363, 1368 (Cl. Ct. 1989), the word "substantially" in patent claims gives rise to some definitional leeway—thus the word "substantially" may prevent avoidance of infringement by minor changes that do not affect the results sought to be accomplished.

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Some aspects of the teachings of the present disclosure may be expressed as a filtering needle assembly for use in administering a liquid payload, the filtering needle assembly comprising: a needle and connector portion; a filter needle cap body; a seal plug, and a filter. The needle and connector portion includes a hollow needle with a distal tip of the hollow needle having an opening to a lumen running through the hollow needle. The needle and connector portion also includes a hub which in turn includes:

an open proximal end adapted to reversibly engage a fluid fitting; and a distal end of the hub engaged with a proximal end of the hollow needle.

The filter needle cap body includes a distal open end in fluid communication via an internal channel with a proximal open end of the filter needle cap body. The proximal open end of the filter needle cap body is sized to receive the distal end of the hub within the proximal open end of the filter needle cap body to reversibly engage the hub when the distal end of the hollow needle is inserted into the internal channel.

The filtering needle cap also includes a filter adapted for removing debris from the liquid payload as the liquid payload is drawn through the filter and the filtering needle cap into the lumen within the hollow needle as the liquid payload is drawn into the fluid fitting.

The filtering needle assembly also includes a seal plug to surround a distal portion of the hollow needle after the distal tip of the hollow needle is pushed through the seal plug to form a seal between the seal plug and the distal portion of the hollow needle so that the liquid payload is drawn into the lumen in the hollow needle as the liquid payload is drawn into the fluid fitting and is blocked by the seal plug from traveling down an outside diameter of the hollow needle within the filtering needle cap.

In this sort of filtering needle assembly, removing the hollow needle from the seal plug precludes reliable reinsertion of the hollow needle through the seal plug as subsequent contact of the distal end of the hollow needle pushes the seal plug towards the distal open end of the filter needle cap body to preclude a second use of the filtering needle assembly.

Some aspects of the teachings of the present disclosure may be expressed as a method for loading a quantity of a filtered liquid payload into a syringe and a connected hollow needle and precluding loading a second quantity of filtered liquid payload into a second syringe and connected second hollow needle. The method includes:
  obtaining a reservoir of a liquid payload; and
  obtaining the syringe attached to a filtering needle assembly, the filtering needle assembly comprising: a needle and connector portion and a filter needle cap body:
  The needle and connector portion including:
  a hollow needle with a distal tip of the hollow needle having an opening to a lumen running through the hollow needle; and
  a hub that includes an open proximal end adapted to reversibly engage a fluid fitting; and a distal end of the hub engaged with a proximal end of the hollow needle.
  The filter needle cap body including:
  a distal open end in fluid communication via an internal channel with a proximal open end of the filter needle cap body;
  the proximal open end of the filter needle cap body sized to receive the distal end of the hub within the proximal open end of the filter needle cap body to reversibly engage the hub when the distal end of the hollow needle is inserted into the internal channel;
  a filter adapted for removing debris from the liquid payload as the liquid payload is drawn through the filtering needle assembly into the lumen within the hollow needle as the liquid payload is drawn into the fluid fitting; and
  a seal plug to surround the distal end of the hollow needle after the distal end of the hollow needle has been driven through the seal plug to form a seal between the seal plug and a distal portion of the hollow needle so that the liquid payload is drawn into the lumen in the hollow needle as the liquid payload is blocked by the seal plug from traveling down an outside diameter of the hollow needle within the filter needle cap body.

The seal plug held in place by a tool as the distal tip of the hollow needle is driven through the seal plug as the seal plug is able to move distally and away from the distal end of the hollow needle unless held in place by the tool so that a second hollow needle cannot be used to load a second quantity of a second filtered liquid payload into a second syringe after removal of the hollow needle from the seal plug.

The method for loading a quantity of a filtered liquid payload into a syringe using the syringe to draw in the liquid payload from the reservoir of the liquid payload also including using the syringe to draw in the liquid payload from the reservoir of the liquid payload, the liquid payload passing through the filter before entering the opening in the distal end of the hollow needle before removing the hollow needle from the filtering needle assembly to expose the distal tip of the hollow needle.

Some aspects of the teachings of the present disclosure may be expressed as a method of assembling a filtered needle assembly. This method includes obtaining
  a needle and connector portion;
  a filtering needle cap body;
  a seal plug; and
  a filter.

This method includes pushing the seal plug into an open distal end of the filtering needle cap body until the seal plug rests against an annular shoulder at a distal end of a proximal chamber that lies between the annular shoulder and an open proximal end of the filtering needle cap body.

This method includes holding the seal plug against the annular shoulder with a holding tool that has an open midline while advancing a distal tip of a hollow needle through the seal plug so that the distal tip of the hollow needle extends beyond a distal end of the seal plug and into the open midline of the holding tool.

The method then calls for removing the holding tool after the distal tip of the hollow needle extends beyond the distal end of the seal plug.

The method then calls for inserting the filter into the distal end of the filtering needle cap body and securing the filter to the distal end of the filtering needle cap body.

Some aspects of the teachings of the present disclosure may be expressed as a method for making a filtered needle assembly unable to work with a hollow needle. While counterintuitive to design to fail, this precludes a second use of a filtered needle assembly and thus protects the patients from improvident second uses of a filtered needle assembly. The method can be summarized as loading a syringe with a liquid payload through a filtering needle assembly then retaining rather than discarding the filtering needle assembly.

Subsequently inserting a distal tip of a hollow needle into an open proximal end of the filtering needle assembly and advancing the distal tip of the hollow needle through a proximal chamber of the filtering needle assembly and into a hollow interior of a seal plug.

The method also calls for advancing the distal tip of the hollow needle distally until contact with the seal plug pushes the seal plug distally within a distal chamber of the filtering needle assembly without traversing the seal plug. The result is that someone attempting to use the filtering needle assembly will end up failing to easily draw liquid into the hollow needle as the distal tip of the hollow needle is not in the distal chamber as the distal tip of the hollow needle could not pass through the seal plug without a holding tool holding the seal plug against an annular shoulder at a distal end of a proximal chamber.

Additional aspects of the teachings of the present disclosure may be expressed as a method of assembling a filtered needle assembly that includes obtaining
- a needle and connector portion;
- a filtering needle cap body;
- a seal plug; and
- a filter.

The method also includes pushing the seal plug into an open distal end of the filtering needle cap body until the seal plug rests against an annular shoulder at a distal end of a proximal chamber that lies between the annular shoulder and an open proximal end of the filtering needle cap body.

Subsequently, holding the seal plug against the annular shoulder with a holding tool that has an open midline while advancing a distal tip of a hollow needle through the seal plug so that the distal tip of the hollow needle extends beyond a distal end of the seal plug and into the open midline of the holding tool.

Then, removing the holding tool after the distal tip of the hollow needle extends beyond the distal end of the seal plug before inserting the filter into the distal end of the filtering needle cap body and securing the filter to the distal end of the filtering needle cap body.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 7 illustrates process 1000 for loading a syringe with a liquid payload through a filtered needle assembly 100.

FIG. 8 illustrates process 2000 for precluding loading second syringe with a previously used filtered needle assembly 100.

FIG. 10 sets forth the key steps in the process 3000 to assemble a filtered needle assembly 100.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
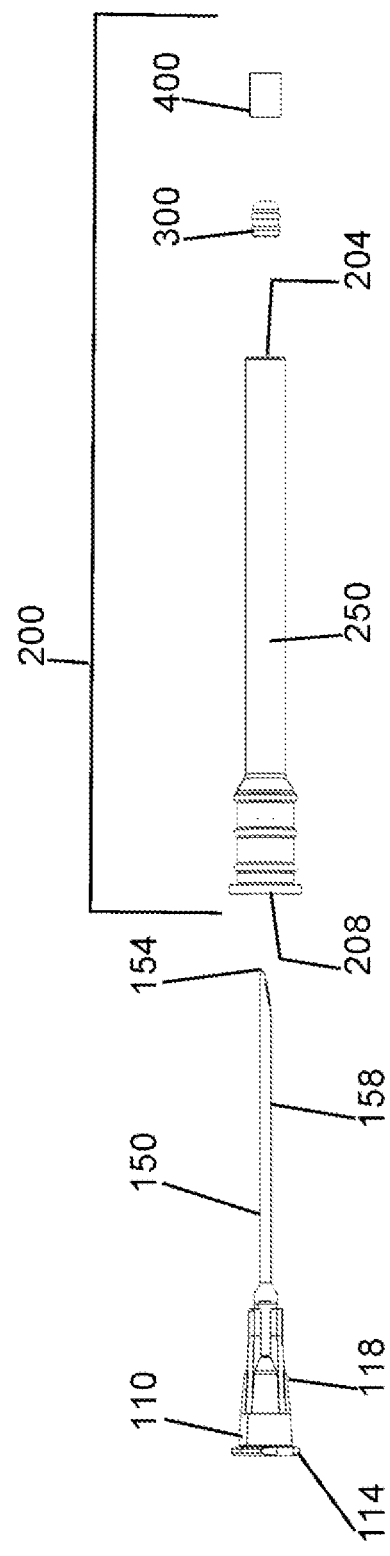
FIG. 1 illustrates the filtered needle assembly 100 in exploded perspective form.

FIG. 1 illustrates the filtered needle assembly 100 in exploded perspective form. Introduced in FIG. 1 are: the needle and connector portion 110 and a filtering needle cap 200, which includes a seal plug 300, and a filter 400.

The needle and connector portion 110 has a proximal end 114 which may be in the form of a hub 118. The hub 118 may be adapted to work with a Luer fitting sometimes called a Luer Taper. Luer fittings include those known as Luer-Lock and Luer-Slip (sometimes slip tip). While various Luer fittings are very common connections for medical devices, the teachings of the present disclosure are not limited to any specific fitting as other connections could be used.

Frequently, but not always, the connection between the hollow needle 150 and the hub 118 is augmented by an adhesive component. Such an adhesive component is conventional and not a point of focus for the present disclosure. Thus, details of this adhesive component are not provided. The adhesive component may be considered a part of the hub 118 for the purposes of this disclosure and the claims that follow.

The hollow needle 150 is secured to the hub 118 of the needle and connector portion 110. The hollow needle 150 has a distal tip 154 that is fluid communication with a needle lumen 156. As discussed below, this application teaches sealing around a distal portion 158 of the hollow needle 150. The distal portion 158 includes the distal tip 154 but also a nearby portion of the hollow needle 150 so that the distal tip 154 extends beyond the sealed portion of the distal portion 158 of the hollow needle 150.

The filtering needle cap 200 has a filter needle cap body 250 with a distal portion 204 which is open, and a proximal end 208 which is also open. The filtering needle cap 200 also has a seal plug 300 and a filter 400 which are inserted into the open distal portion 204 of the filter needle cap body 250 during assembly.

Figure 2:
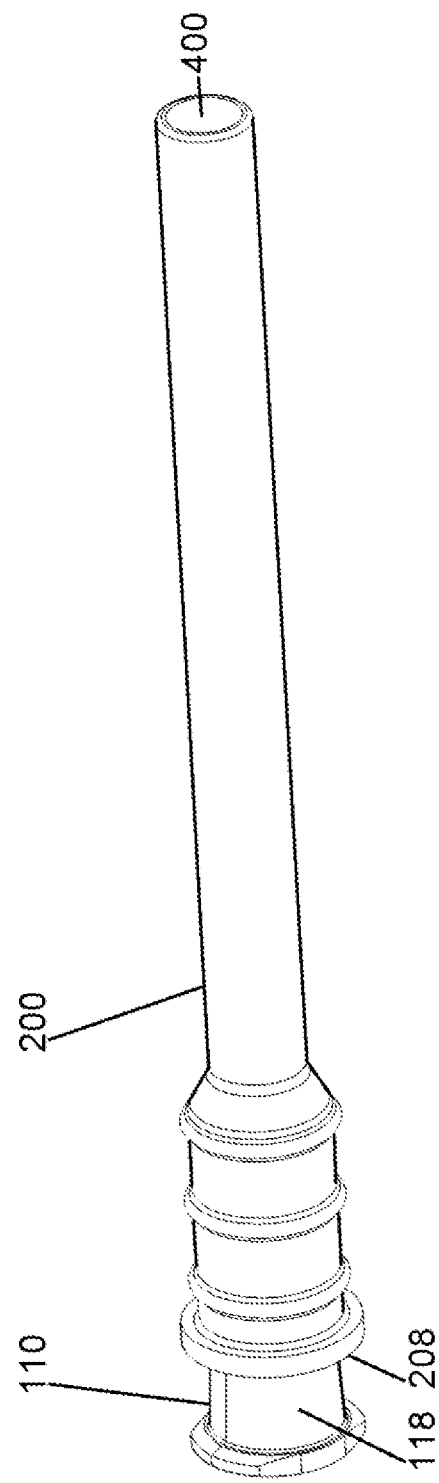
FIG. 2 is a side and front perspective view of filtered needle assembly 100 which allows a view of the filter 400 within the distal end of the filtered needle assembly 100.

FIG. 2 is a side and front perspective view of filtered needle assembly 100 which allows a view of the filter 400 within the distal end of the filtered needle assembly 100.

A distal portion of the hub 118 is designed to be secured within the open proximal end 208 of the filtering needle cap 200.

Figure 3:
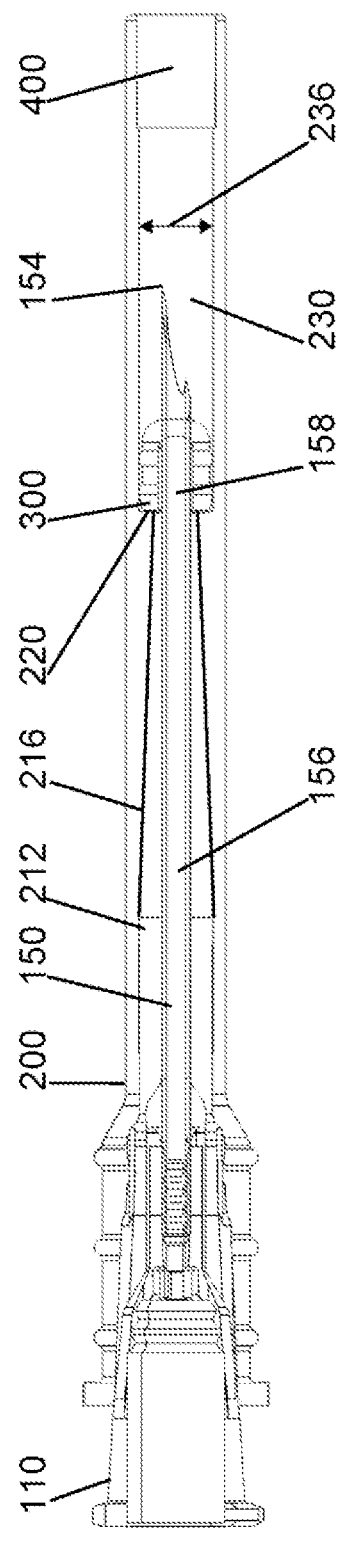
FIG. 3 is a cross section of filtered needle assembly 100.

FIG. 3 is a cross section of filtered needle assembly 100. FIG. 3 shows that the distal tip 154 of the hollow needle 150 may be inserted distally into the open proximal end 208 of the filtering needle cap 200 and advanced through the proximal chamber 212. As the distal tip 154 moves distally, the cross section of the proximal chamber 212 diminishes via inwardly sloped walls 216. Eventually, the distal tip 154 reaches an annular shoulder 220 that limits the proximal movement of the seal plug 300. The annular shoulder 220 is the proximal end of the distal chamber 230.

Figure 4:
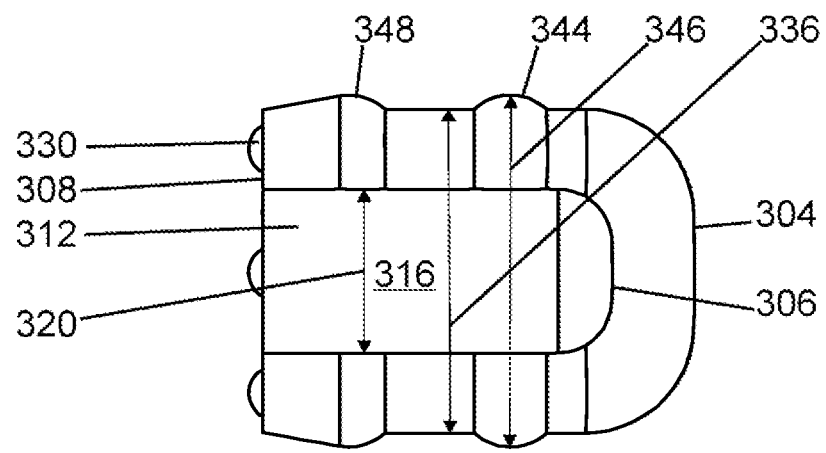
FIG. 4 is a cross section of a side view of the seal plug 300.

FIG. 4 is a cross section of a side view of the seal plug 300. Seal plug 300 has a distal end 304 that is originally closed but later punctured by the distal tip 154 of the hollow needle 150. The seal plug 300 has a proximal face 308 with an opening 312 to a hollow interior 316 that is initially closed at the distal end 306. Optionally, the diameter 320 of most of the hollow interior 316 is greater than the outer diameter of the hollow needle 150 so the distal tip 154 (FIG. 3) of the hollow needle 150 can traverse most of the hollow interior 316 without resistance.

The annular proximal face 308 has a series of hemispheric protrusions 330 which make contact with the annular shoulder 220 of the filtering needle cap 200. These hemispheric protrusions 330 assist in ejecting the molded parts from the mold.

The seal plug 300 has a first rib ring 344 and a second rib ring 348. A careful observer will note that in this instance, the first rib ring 344 is not the same shape as the second rib ring 348. Both rib rings (344 and 348) have a maximum outer diameter 346 that is larger than outer diameter 336. The maximum outer diameter 346 of the rib rings (344 and 348) is larger than the inner diameter 236 of distal chamber 230 (FIG. 3). Thus, when seal plug 300 is loaded into the distal chamber 230 before the addition of the filter 400, a holding tool can be used to push the seal plug 300 proximally as the rib rings (344 and 348) compress to fit within inner diameter 236 of distal chamber 230. This compression fit retains the seal plug 300 in proximity to the annular shoulder 220 at the proximal end of the distal chamber 230.

The holding power of this compression fit is not sufficient to resist force imposed by a distal tip 154 of a hollow needle 150 if the hollow needle 150 is advanced distally. The hollow needle 150 pushes the seal plug 300 distally away from the annular shoulder 220 at the proximal end of the distal chamber 230.

Use of a Holding Tool.

While a wide range of holding tools could be used to move the seal plug 300 proximally within the distal chamber 230, a holding tool with an open midline may be used to retain the seal plug 300 against the annular shoulder 220 at the proximal end of the distal chamber 230 as the distal tip 154 of the hollow needle 150 is pushed against the initially closed distal end 306 of the hollow interior 316 of the seal plug 300.

With an appropriate holding tool holding the seal plug 300 against the annular shoulder 220 at the proximal end of the distal chamber 230, sufficient force can be applied to the hollow needle 150 to drive the distal tip 154 through the remainder of seal plug 300 and out the distal end 304 of the seal plug 300 so that a seal is formed around distal portion 158 (FIG. 3) of the hollow needle 150.

After removing the holding tool and inserting the filter 400, one has a filtered needle assembly 100 as shown in FIG. 2 and FIG. 3.

Additional Views of Seal Plug.

Figure 5:
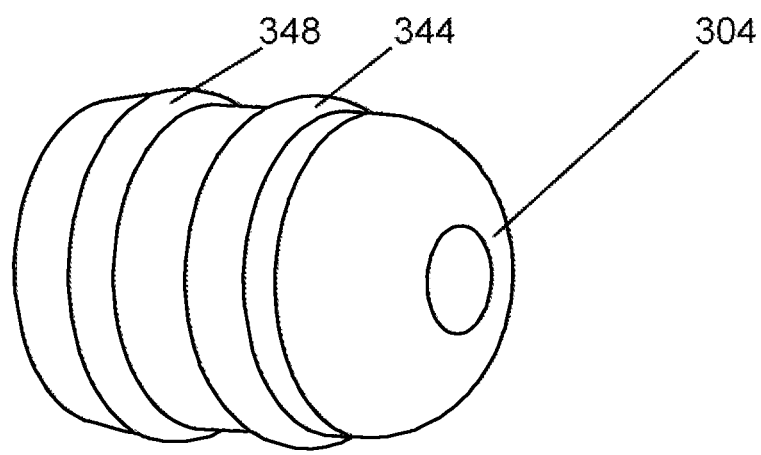
FIG. 5 provides a front side perspective view of seal plug 300.

FIG. 5 provides a front side perspective view of seal plug 300. Visible in this view are distal end 304, first rib ring 344 and second rib ring 348. The circle visible at the distal end 304 is simply a flat portion of the domed distal end 304.

Figure 6:
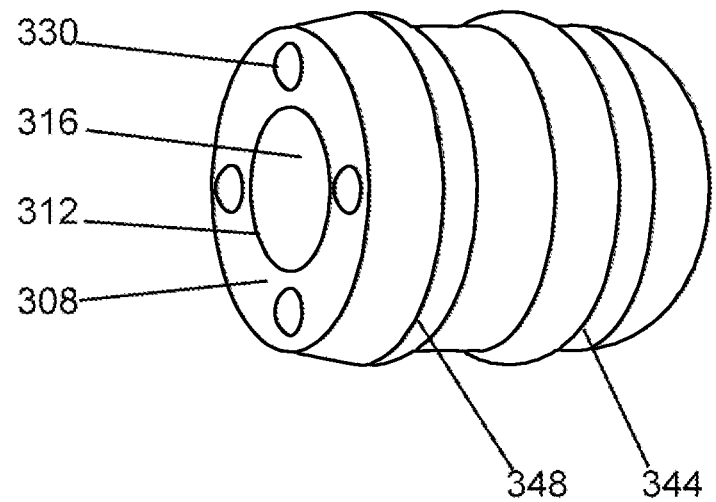
FIG. 6 provides a rear side perspective view of seal plug 300.

FIG. 6 provides a rear side perspective view of seal plug 300. Visible in this view are proximal face 308, opening 312, a portion of hollow interior 316, and the set of hemispheric protrusions 330. Also visible in this view are first rib ring 344 and second rib ring 348

Process for Use.

FIG. 7 illustrates process 1000 for loading a syringe with a liquid payload through a filtered needle assembly 100.

Step 1004—Add Filtered Needle Assembly to Syringe. The filtered needle assembly 100 such as shown in FIG. 2 is secured to the end of a syringe (not shown) or other fitting by engagement with the hub 118 at the proximal end 114 of the needle and connector portion 110.

Step 1008—Optional—Remove Outer Cap. Often, the filter needle assembly 100 is shipped with an outer cap (not shown here). The outer cap is removed. Note this step is optional as in some instances the filter needle may be delivered in sterile packaging such as a blister pack without an outer cap. In many instances the filter needle assembly will be delivered with the needle and connector portion 110 factory inserted into the filtering needle cap 200 and with the outer cap covering a portion of the filtering needle cap 200. In order to minimize the chances that the filtering needle cap 200 will be separated from the needle and connector portion 110 when intending to merely remove the outer cap, the components may be designed so that the force needed to remove the filtering needle cap 200 from the needle and connector portion 110 may be significantly more than the force needed to remove the outer cap from the filtering needle cap 200. In this context, significantly more would include at least double. The difference in required force may be achieved by having different degrees of interference fits, or use of different materials or surface treatments. Other ways of increasing or decreasing the requisite removal force will be apparent to those of skill in the art.

Step 1012—Draw Payload into Syringe. The filter element 400 is immersed in an ampoule or suitable receptacle for a liquid payload such as a pharmaceutical or other liquid. As the syringe plunger is withdrawn in a known manner, the liquid payload is drawn up in order to fill the syringe through a pathway through:
  the filter element 400;
  the distal chamber 230; and
  the interior of the hollow needle 150 that extends beyond the seal plug 300 into the distal chamber 230.

The suction force for drawing up the liquid payload is confined to the pathway by the seal plug 300 which substantially seals the distal chamber 230. The seal plug 300 prevents the flow of air in a distal direction from entering the distal chamber 230 from along the outer perimeter of the hollow needle 150 such that the syringe may effectively draw in liquid payload. As the syringe is loaded, any debris in the receptacle initially holding the liquid payload is precluded by the filter element 400 from entry into the distal chamber 230.

Step 1016—Remove Filtered Needle Assembly from Syringe. Once the syringe is loaded, the filtering needle cap 200 is removed from the needle and connector portion 110 by sliding the filtering needle cap 200 distally until the distal tip 154 of the hollow needle 150 is free of the filtering needle cap 200. The filtering needle cap 200 may then be discarded along with any debris captured in the filter 400.

Step 1020—Loaded Syringe is Ready for Use. The syringe is loaded with the desired amount of liquid payload which has been filtered as the liquid passed through filter 400. The distal tip 154 of the hollow needle 150 is exposed and ready for use. Depending on the application, the distal tip 154 of the hollow needle 150 may be inserted as appropriate into a patient's body, to a port with a septum for use with IV therapy, or to some other location.

Process for Precluding Second Use.

FIG. 8 illustrates process 2000 for precluding loading second syringe with a previously used filtered needle assembly 100.

Step 2004—Load a syringe with a liquid payload through a filtered needle assembly 100 including a filtering needle cap 200 as described in process 1000 but do not discard the filtering needle cap 200 after removing the hollow needle 150 from the filtering needle cap 200.

Step 2008—Insert a distal tip of a hollow needle into the open proximal end of the filtering needle cap 200. This distal tip of a hollow needle may be the same distal tip of the hollow needle used in process 1000 or may be a new distal tip of a new hollow needle attached to a new syringe.

Step 2012—Advance the distal tip of the hollow needle through the proximal chamber of the filtering needle cap and into the hollow interior 316 of the seal plug 300.

Step 2016—Continue to advance the distal tip of the hollow needle distally.

Step 2020—Contact the distal tip 154 of the hollow needle 150 with the seal plug 300. As the opening formed by forcing the first distal tip of the first hollow needle across the seal plug 300 while the seal plug 300 was precluded from distal movement by an appropriate holding tool has substantially closed after withdrawal of the hollow needle from the seal plug 300, there is resistance even if the second distal tip 154 is perfectly aligned with the prior path taken by the first distal tip 154.

Figure 9:
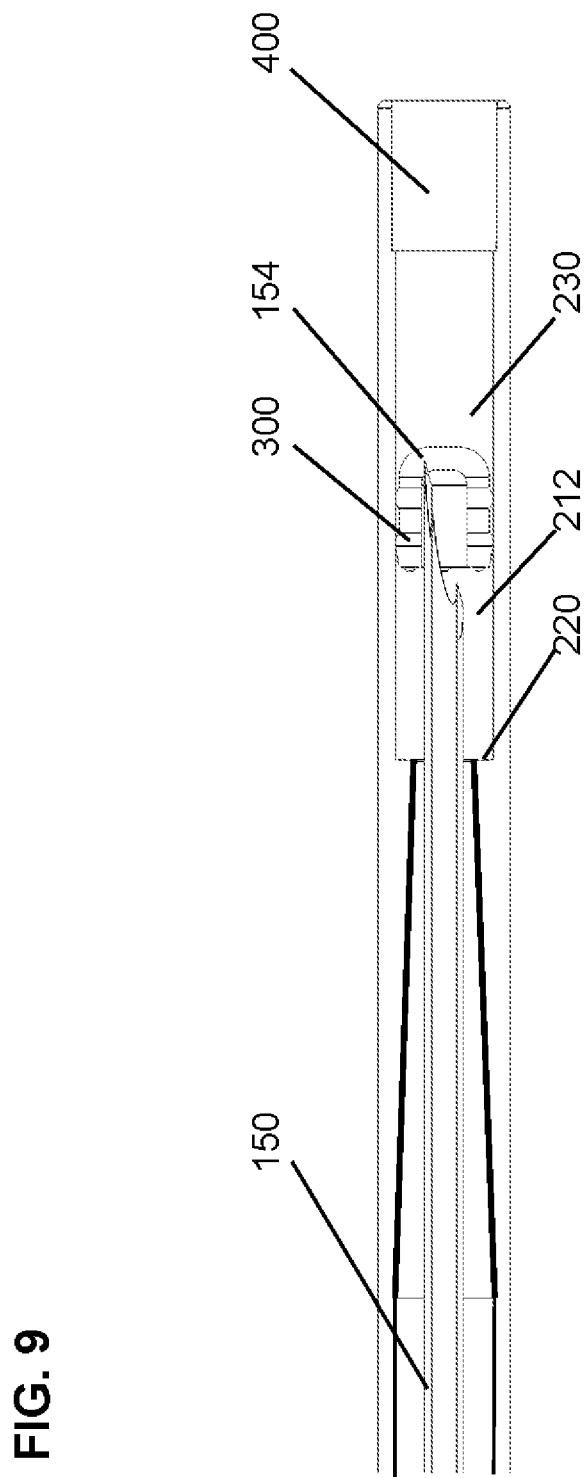
FIG. 9 shows an enlarged partial cross section of the filter needle assembly 100 after a distal tip 154 of a hollow needle 150 has pushed against the seal plug 300 while not held by a holding tool.

Step 2024—Push the seal plug 300 distally within the distal chamber without traversing the seal plug 300. As the force needed to penetrate and traverse the seal plug is greater than the friction force holding the seal plug 300 adjacent to the annular shoulder 220 by the compression fit of the rib rings (344 and 348) within the distal chamber 230, the continued distal movement of the distal tip 154 of the hollow needle 150 pushes the seal plug 300 distally within the distal chamber without traversing the seal plug 300. See FIG. 9 which shows an enlarged partial cross section of the filter needle assembly 100 after a distal tip 154 of a hollow needle 150 has pushed against the seal plug 300 while not held by a holding tool. The seal plug 300 has slid distally within distal chamber 230.

Step 2028—Fail to easily draw in liquid payload through filter 400 as the distal tip 154 of the needle 150 has not traversed the seal plug 300. It is possible that some liquid payload may eventually be drawn through the prior needle path in the seal plug 300 but it is likely that air from the proximal end of the filter needle assembly 100 would travel down to the distal tip 154 of the hollow needle 150 as the distal tip is on the proximal side of the seal and nothing would block air from entering the distal tip and satisfying the suction pull from the syringe body. This would not be a satisfactory process and the staff member would not try this a second time. Thus the design precludes making a habit of loading second syringe with a previously used filtered needle assembly 100 as the hollow needle displaces rather than traverses the seal plug and does not work well to obtain liquid payload.

The process set forth above precludes insertion of a second hollow needle connected to a second syringe to draw up a second payload liquid. In this context, the filtering needle cap 200 cannot recognize that the inserted hollow needle 150 is the same hollow needle 150 that was recently withdrawn from the filtering needle cap 200. Once the hollow needle 150 is removed from the filtering needle cap 200, the hollow needle becomes a stranger and thus a second hollow needle connected to a second syringe seeking to obtain a second liquid payload. The process would work the same when a different hollow needle was inserted. That hollow needle would also be treated as a prohibited second hollow needle.

Process for Assembling a Filtered Needle Assembly.

FIG. 10 sets forth the key steps in the process 3000 to assemble a filtered needle assembly 100.

Step 3004—Obtain: the needle and connector portion 110, a filtering needle cap body 25, a seal plug 300, and a filter 400.

Step 3008—Push the seal plug 300 into the open distal end of the filtering needle cap body 250 and continue moving the seal plug 300 until the seal plug rests against the annular shoulder 220 at the end of the proximal chamber 212.

Step 3012—Hold the seal plug while the distal tip traverses the seal plug. More specifically, hold the seal plug 300 against the annular shoulder with a holding tool that has an open midline while advancing the distal tip 154 of the hollow needle 150 all the way into the hollow interior 316 of the seal plug 300 and then push the distal tip 154 through the remaining portion of the seal plug 300 while the seal plug 300 is precluded from distal movement by the holding tool so that the distal tip 154 extends beyond the distal end 304 of the seal plug 300 and into the empty midline of the holding tool.

Step 3016—Remove the holding tool from the distal portion 204 of the filtering needle cap after the distal end of the hollow needle extends beyond the distal end of the seal plug.

Step 3020—Insert the filter 400 into the distal end of the filtering needle cap body 250. The filter may be held in position by various methods known to those of skill in the art including adhesives, compression fit, and others.

Step 3024—Creating a sealed and sterilized package with the filtered needle assembly 100 inside the package.

Details

Choice of Filter Element.

One design criterion for choice of a filter element on the distal end of the filtering needle cap versus a filter element contained internal in the filtering needle cap is whether collection of abnormal components within the liquid payload is relevant to the application. While all filter elements may be used to remove shards of glass, in some instances it may be useful to use a filter element on the distal end of the filtering needle cap as this distal surface will concentrate certain types of abnormal components. For example, some pharmaceuticals may partially crystalize from age or handling. While a small amount of crystallization may be tolerated, an unusual amount of crystallization may indicate that the pharmaceutical should be discarded rather than used. Likewise, some pharmaceuticals may have a small amount of sediment in the reservoir of the pharmaceutical such as an ampoule, but if a large amount of sediment appears on the outer surface of the filter element, the excessive sediment may indicate that the pharmaceutical is too old or has been compromised by handling.

The filter elements may be sintered filters which have a number of tortuous internal channels for liquid payload to traverse while capturing debris. Extending the thickness of the filter increases the distance that the liquid payload must travel but it also increases the number of possible paths for the liquid payload to travel. Thus, for some range of thicknesses, increasing the thickness decreases the overall resistance to flow.

One well-known vendor in the field of sintered filter material is the Porex Corporation located in Fairburn Georgia and at www.Porex.com (spaces inserted to avoid a live link).

Material for Plug.

The choice of the material for use in the plug will be a design choice and may be influenced by the type of needle being used and the geometry of the plug and other components. The material will need to be compatible with the liquids to be filtered, planned sterilization process, and desired shelf life. One suitable material is 50 durometer Chlorobutyl which is available from a number of vendors.

Retention of the Filter Element.

In some of the examples set forth above, the filter element was retained by protrusions or detents that extended into the filter element to secure the filter element. Adhesives may be used to secure the filter element. Many designers may prefer a protrusion or other form of interference fit as the use of adhesives might cause adhesives to enter possible flow paths for liquid payload and thus partially impair the filter element. Those of skill in the art will recognize that other attachment methods may be used such at an ultrasonic bond, spin welding, heat welding, and press fit. Likewise, other suggested connections between components have been provided to provide a suitable example and those of skill in the art will recognize the many options for connecting two components together. The teachings of this present disclosure are not limited to any particular connection method for joining components unless specifically recited in the claims that follow.

Needle Types.

The various figures discussed in connection with this disclosure have uniformly shown sharp distal ends for the needles. These needles have beveled tips. Sharp ended hypodermic needles are particularly adapted for injecting fluids directly into the body of the patient.

In many instances, the liquid payload is not delivered directly into the patient but is instead delivered to a bag of fluids used in intravenous therapy (IV therapy). A drip of liquid is provided into a vein of the patient to slowly provide a desired treatment. The IV fluids are typically in a bag. Ports with a self-sealing septum may be used to add pharmaceuticals to the liquid being provided in IV therapy. While a sharp tipped needle may be used to deliver a liquid payload through a septum, some prefer using a blunt tip needle. A blunt tip needle reduces the risk of a needle stick to the medical personnel and may be less damaging to the septum. While the variation of needle tips and the best uses for each type of needle tip are beyond the scope of the present disclosure, nothing in this present disclosure limits the teachings to applications with sharp point needles. Blunt tip needles will have openings on their distal portions and one of skill in the art can adapt the geometries of the filtering needle cap if needed to accommodate the geometry of various types of blunt tip needles.

Connection to the Hub.

The examples in this disclosure referenced a distal end of a syringe engaging with the hub 118. This may be the most common interaction with the filter needle, but the teachings of this disclosure could be employed where there is a combination of components rather than a syringe. For some specific reasons, there may be a series of components including check valves, tubing, a syringe, or even a replacement for a syringe that may controllably intake and discharge liquid payload through the needle. The present disclosure may be used as long as there is an appropriate connection between the filtered needle and the remaining components via the distal fluid fitting of the remaining components.

Sterilization Choices.

Those of skill in the art will recognize that the filtering needle cap with or without an outer cap may be sterilized prior to provision to the medical facility. Those of skill in the art will recognize that there are many different processes such as electron beam processing, gamma ray sterilization, or ethylene oxide gas. Those of skill in the art will recognize that medical devices may be adapted for use with a particular sterilization process to maximize effectiveness and throughput. The teachings of the present disclosure may be adapted for use with a variety of sterilization techniques and thus this aspect of the examples was not highlighted or discussed.

Optional Use of Outer Cap.

As noted above, some applications may not use the outer cap but package the needle and connector portion along with the filtering needle cap in packaging such as a blister pack. The packaging would maintain the sterility of the items and would preclude even sterilized debris from becoming entrained in the filtering needle cap. Outer caps are well known to those of skill in the art. FIG. 1 of U.S. Pat. No. 9,669,164 shows an outer cap as element 12. FIG. 1 is incorporated by reference.

Alternatives and Variations.

Locations of the filter 400.

While the figures used in the present disclosure show a filter 400 wholly within the distal end of the filtering needle cap 200, this is not required in order to enjoy the benefits of the seal plug 300. U.S. Pat. No. 9,669,164 to Carr et al. for Filtering Needle Cap Having a Sleeve Sealing Around a Needle shows a range of suitable locations for the filter. The '164 patent is incorporated by reference in its entirety.

Number of Rib Rings.

The example set forth above had a seal plug 300 with two rib rings 344 and 348. One of skill in the art will appreciate that the number of rib rings could be one, two, or more than two. What is needed is an ability to push the seal plug 300 into a slightly smaller diameter as the seal plug 300 deforms to fit and this compression fit increases the amount of force necessary to move the seal plug 300 but does not raise the required level sufficiently to allow a distal tip 154 of a hollow needle 150 to be driven through a seal plug 300 without the use of a holding tool.

Holding Tool.

Figure 11:
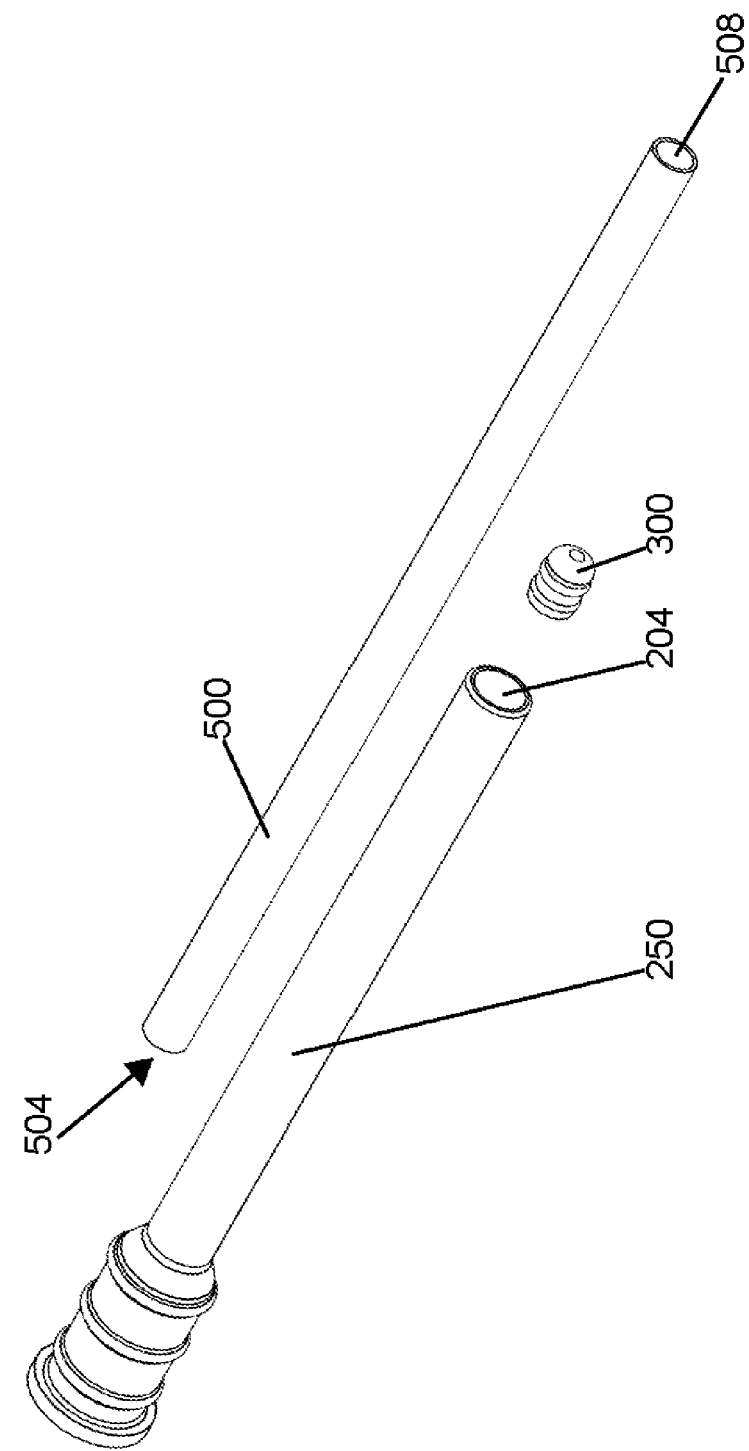
FIG. 11 provides a perspective view of holding tool 500, the filter needle cap body 250 and the seal plug 300.

FIG. 11 provides a perspective view of holding tool 500, the filter needle cap body 250 and the seal plug 300. The holding tool 504 has a distal end 508 and a proximal end 504 which is inserted into the open distal portion 204 of the filter needle cap body 250 and then used to push and hold the seal plug 300 against the annular shoulder 220 (FIG. 3). While the seal plug 300 is held against the annular shoulder 220, the distal tip 154 of the hollow needle 150 (FIG. 3) may be forced to penetrate and transit the distal end 304 (FIG. 4) of the seal plug 300.

The proximal end 504 of the holding tool 500 needs a concavity of sufficient depth to receive the distal end of the hollow needle 150 that extends beyond the distal end 304 of the seal plug 300. One way to form this concavity is to have a holding tool 500 that is a hollow cylinder with an open midline from the proximal end 504 to the distal end 508. But this is not required. The opening at the proximal end 504 may end somewhere within the holding tool 500. The proximal end 504 of the holding tool may be a set of two or more fingers that hold the seal plug 300 against the annular shoulder 220 and provide adequate room for the distal end of the hollow needle 150. Those of skill in the art can work with the present disclosure to come up with a variety of holding tools in keeping with the purpose of the tool.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

Where methods and/or events described above indicate certain events and/or procedures occurring in a certain order, the ordering of certain events and/or procedures may be modified. Additionally, certain events and/or procedures may be performed concurrently in a parallel process, when possible, as well as performed sequentially as described above. The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A filtering needle assembly (100) for use in administering a liquid payload, the filtering needle assembly comprising: a needle and connector portion (110); a filter needle cap body (250); a seal plug (300), and a filter (400):
   the needle and connector portion (110) comprising:
      a hollow needle (150) with a distal tip (154) of the hollow needle having an opening to a lumen (156) running through the hollow needle; and
      a hub (118) comprising:
         an open proximal end (114) adapted to reversibly engage a fluid fitting; and
         a distal end of the hub engaged with a proximal end of the hollow needle; and
   the filter needle cap body (250) comprising:
      a distal open end (204) in fluid communication via an internal channel with a proximal open end of the filter needle cap body;
      the proximal open end (208) of the filtering needle assembly sized to receive the distal end of the hub within the proximal open end of the filter needle cap body to reversibly engage the hub when the distal end of the hollow needle is inserted into the internal channel;
      the filter (400) adapted for removing debris from the liquid payload as the liquid payload is drawn through the filter and the filtering needle assembly into the lumen within the hollow needle as the liquid payload is drawn into the fluid fitting; and
      the seal plug (300) to surround a distal portion of the hollow needle after the distal tip of the hollow needle is pushed through the seal plug to form a seal between the seal plug and the distal portion of the hollow needle so that the liquid payload is drawn into the lumen in the hollow needle as the liquid payload is drawn into the fluid fitting and is blocked by the seal plug from traveling down an outside diameter of the hollow needle within the filtering needle assembly; and
   wherein removing the hollow needle from the seal plug precludes reliable reinsertion of the hollow needle through the seal plug as subsequent contact of the distal end of the hollow needle pushes the seal plug towards the distal open end of the filter needle cap body to preclude a second use of the filtering needle assembly.

2. The filtering needle assembly of claim 1 wherein the seal plug is dome shaped with a convex shape on a distal end (304) of the seal plug and a hollow interior (316) open at a proximal face (308) of the seal plug so that the distal tip of the hollow needle may travel through the hollow interior before being pushed through material between a distal end (306) of the hollow interior and the distal end (304) of the seal plug.

3. The filtering needle assembly of claim 1 wherein the seal plug has at least one rib ring (344, 348) so that an outer diameter of the seal plug is not constant from a proximal end of the seal plug to the distal end of the seal plug and the at least one rib ring forms a friction fit with a seal plug portion of an interior of the filter needle cap body where the seal plug is held while the distal end of the hollow needle is pushed through the seal plug so that the liquid payload is substantially blocked from traveling between the at least one rib ring and the seal plug portion of the interior of the filter needle cap body.

4. The filtering needle assembly of claim 1 further comprising an outer cap with a closed distal end which may be placed over at least a portion of the filtering needle assembly until the filtering needle assembly is uncovered for filtering the liquid payload as the liquid payload is drawn into the fluid fitting.

5. The filtering needle assembly of claim 1 wherein the open proximal end of the hub is adapted to be reversibly engaged with the fluid fitting on a distal end of a syringe such that:
   operation of the syringe to intake the liquid payload that was filtered by the filter and then passes through the hollow needle; and
   subsequent removal of the filtering needle assembly to expose the distal end of the hollow needle allows administration of a volume of filtered liquid payload through operation of the syringe.

6. The filtering needle assembly of claim 1 provided in a kit with a reservoir of the liquid payload for administration to a patient using the hollow needle after the liquid payload has been filtered.

7. A method for loading a quantity of a filtered liquid payload into a syringe and a connected hollow needle (150) and precluding loading a second quantity of filtered liquid payload into a second syringe connected to a second hollow needle, the method comprising:
   obtaining a reservoir of a liquid payload;
   attaching the syringe to a filtering needle assembly (100), the filtering needle assembly comprising: a needle and connector portion (110) and a filtering needle cap (200):
   the needle and connector portion (110) comprising:
      a hollow needle (150) with a distal tip (154) of the hollow needle having an opening to a lumen (156) running through the hollow needle; and
      a hub comprising:
         an open proximal end (114) adapted to reversibly engage a fluid fitting; and
         a distal end of the hub engaged with a proximal end of the hollow needle; and the filtering needle cap (200) comprising:
- a filtering needle cap body (250) with a distal open portion (204) in fluid communication via an internal channel with a proximal open end (208) of the filter needle cap body; and
- the proximal open end of the filter needle cap body sized to receive the distal end of the hub within the proximal open end of the filter needle cap body to reversibly engage the hub when the distal end of the hollow needle is inserted into the internal channel,
- a filter (400) adapted for removing debris from the liquid payload as the liquid payload is drawn through the filtering needle assembly into the lumen within the hollow needle as the liquid payload is drawn into the fluid fitting; and
- a seal plug (300) to surround the distal end of the hollow needle after the distal end of the hollow needle has been driven through the seal plug to form a seal between the seal plug and a distal portion of the hollow needle so that the liquid payload is drawn into the lumen in the hollow needle as the liquid payload is blocked by the seal plug from traveling down an outside diameter of the hollow needle within the filter needle cap body;
- the seal plug held in place by a holding tool (500) as the distal tip of the hollow needle is driven through the seal plug as the seal plug is able to move distally and away from the distal end of the hollow needle unless held in place by the holding tool so that the second hollow needle cannot be used to load the second quantity of the filtered liquid payload into the second syringe after removal of the hollow needle from the seal plug;
- using the syringe to draw in the liquid payload from the reservoir of the liquid payload, the liquid payload passing through the filter before entering the opening in the distal end of the hollow needle; and
- removing the hollow needle from the filtering needle assembly to expose the distal tip of the hollow needle.

8. The method of claim 7 wherein the syringe with the connected hollow needle becomes the second syringe with the second hollow needle once the hollow needle is removed from the seal plug such that the second hollow needle is now unable to traverse the seal plug.

9. The method of claim 7 wherein the filtering needle assembly is initially sheathed in an outer cap and a force required to remove the outer cap from the filtering needle assembly is less than half of a force needed for removing the needle and connector portion from the filtering needle assembly to expose the distal end of the hollow needle.

10. The method of claim 7 wherein the liquid payload is delivered through a septum for use in IV therapy.

11. A method of assembling a filtered needle assembly (100) comprising:
- obtaining:
  - a needle and connector portion (110);
  - a filtering needle cap body (250);
  - a seal plug (300); and
  - a filter (400);
- pushing the seal plug into an open distal end (204) of the filtering needle cap body (250) until the seal plug rests against an annular shoulder (220) at a distal end of a proximal chamber (212) that lies between the annular shoulder and an open proximal end (208) of the filtering needle cap body;
- holding the seal plug against the annular shoulder with a holding tool (500) that has an open midline while advancing a distal tip (154) of a hollow needle (150) through the seal plug so that the distal tip of the hollow needle extends beyond a distal end (304) of the seal plug and into the open midline of the holding tool;
- removing the holding tool after the distal tip of the hollow needle extends beyond the distal end of the seal plug; and
- inserting the filter into the distal end of the filtering needle cap body and securing the filter to the distal end of the filtering needle cap body.

12. The method of assembling the filtered needle assembly of claim 11 further comprising creating a sealed and sterilized package with the filtered needle assembly inside the sterilized package.

13. The method of assembling the filtered needle assembly of claim 11 wherein the hollow needle advanced through the seal plug is a sharp needle with a beveled tip.

14. The method of assembling the filtered needle assembly of claim 11 wherein the hollow needle advanced through the seal plug is a blunt needle with an opening on a distal end of the hollow needle but not at the distal tip of the blunt needle.

15. The method of assembling the filtered needle assembly of claim 11 further comprising adding an outer cap that covers the filtered needle assembly.

16. The method of assembling the filtered needle assembly of claim 11 wherein the holding tool is a cylinder that fits within the open distal end of the filtering needle cap body and holds the seal plug against the annular shoulder during the advancing of the distal tip of the hollow needle through the seal plug.

17. A method for making a filtered needle assembly unable to work with a second hollow needle, the method comprising:
- loading a syringe with a liquid payload through the filtered needle assembly (100);
- removing a first distal tip (154) of a first hollow needle (150) attached to the syringe from an open proximal end (208) of the filtered needle assembly;
- subsequently, inserting a second distal tip (154) of the second hollow needle (150) into the open proximal end (208) of the filtering needle assembly;
- advancing the second distal tip of the second hollow needle through a proximal chamber (212) of the filtering needle assembly and into a hollow interior (316) of a seal plug (300);
- advancing the second distal tip of the second hollow needle distally until contact with the seal plug pushes the seal plug distally within a distal chamber (230) of the filtering needle assembly without the second distal tip traversing the seal plug; and
- failing to easily draw liquid into the second hollow needle as the second distal tip of the second hollow needle is not in the distal chamber as the second distal tip of the second hollow needle could not pass through the seal plug without a holding tool (500) holding the seal plug against an annular shoulder (220) at a distal end of the proximal chamber (212).

\* \* \* \* \*